(12) United States Patent
O'Hara et al.

(10) Patent No.: US 9,708,651 B2
(45) Date of Patent: Jul. 18, 2017

(54) DNA POLYMERASE ACTIVITY ASSAYS AND METHODS ENABLING DETERMINATION OF VIABLE MICROBES

(71) Applicant: Zeus Scientific, Inc., Branchburg Township, NJ (US)

(72) Inventors: Shawn Mark O'Hara, Richboro, PA (US); Daniel Zweitzig, Feasterville, PA (US)

(73) Assignee: ZEUS Scientific, Inc., Branchburg, NJ (US)

( * ) Notice: Subject to any disclaimer, the term of this patent is extended or adjusted under 35 U.S.C. 154(b) by 0 days.

(21) Appl. No.: 14/370,752

(22) PCT Filed: Jan. 3, 2013

(86) PCT No.: PCT/US2013/020180
§ 371 (c)(1),
(2) Date: Jul. 3, 2014

(87) PCT Pub. No.: WO2013/103744
PCT Pub. Date: Jul. 11, 2013

(65) Prior Publication Data
US 2015/0004617 A1     Jan. 1, 2015

(51) Int. Cl.
*C12P 19/34*     (2006.01)
*C12Q 1/68*     (2006.01)
*C12Q 1/04*     (2006.01)
*C12Q 1/48*     (2006.01)

(52) U.S. Cl.
CPC .............. *C12Q 1/686* (2013.01); *C12Q 1/04* (2013.01); *C12Q 1/48* (2013.01); *C12Q 1/689* (2013.01); *G01N 2333/91245* (2013.01)

(58) Field of Classification Search
CPC .... C12Q 1/686; C12Q 2521/101; C12Q 1/04; C12Q 1/48; C12Q 1/689; G01N 2333/91245
USPC ........................................................ 435/91.2
See application file for complete search history.

(56) References Cited

U.S. PATENT DOCUMENTS

2013/0196318 A1*   8/2013   O'Hara .................... C12Q 1/04
                                                                435/6.11

FOREIGN PATENT DOCUMENTS

WO    WO 2011/130584 A2    10/2011

OTHER PUBLICATIONS

Zweitzig et al (Nucleic acid Research (Apr. 11, 2012) 40 (14):e109, pp. 1-12.*
Crow et al (Momentum Bioscience, http://www.momentumbio.co.uk/wp/wp-content/uploads/2014/03/ETGA-AST-poster_final.pdf, 2014.*
Schwartz et al (PNAS (2009), 106:48, pp. 20294-20299.*

* cited by examiner

*Primary Examiner* — Cynthia B Wilder
(74) *Attorney, Agent, or Firm* — Graham C. Alig; Wilkinson Law L.L.C.

(57) ABSTRACT

A method for performing a diagnostic assay for the detection of the presence or amount of a microorganism within a sample matrix containing active DNA polymerase, is disclosed. The method utilizes the measurement of DNA polymerase extension activity, wherein the assay comprises the steps of incubating DNA polymerase in the sample matrix with a selected suitable substrate, and performing PCR cycling and detection via the use of a selected suitable nucleic acid probe, thereby to detect endogenous DNA polymerase extension activity in the sample matrix as an indication of the presence or amount of said microorganism.

10 Claims, 8 Drawing Sheets

Figure 8

Table 1

Figure 1:
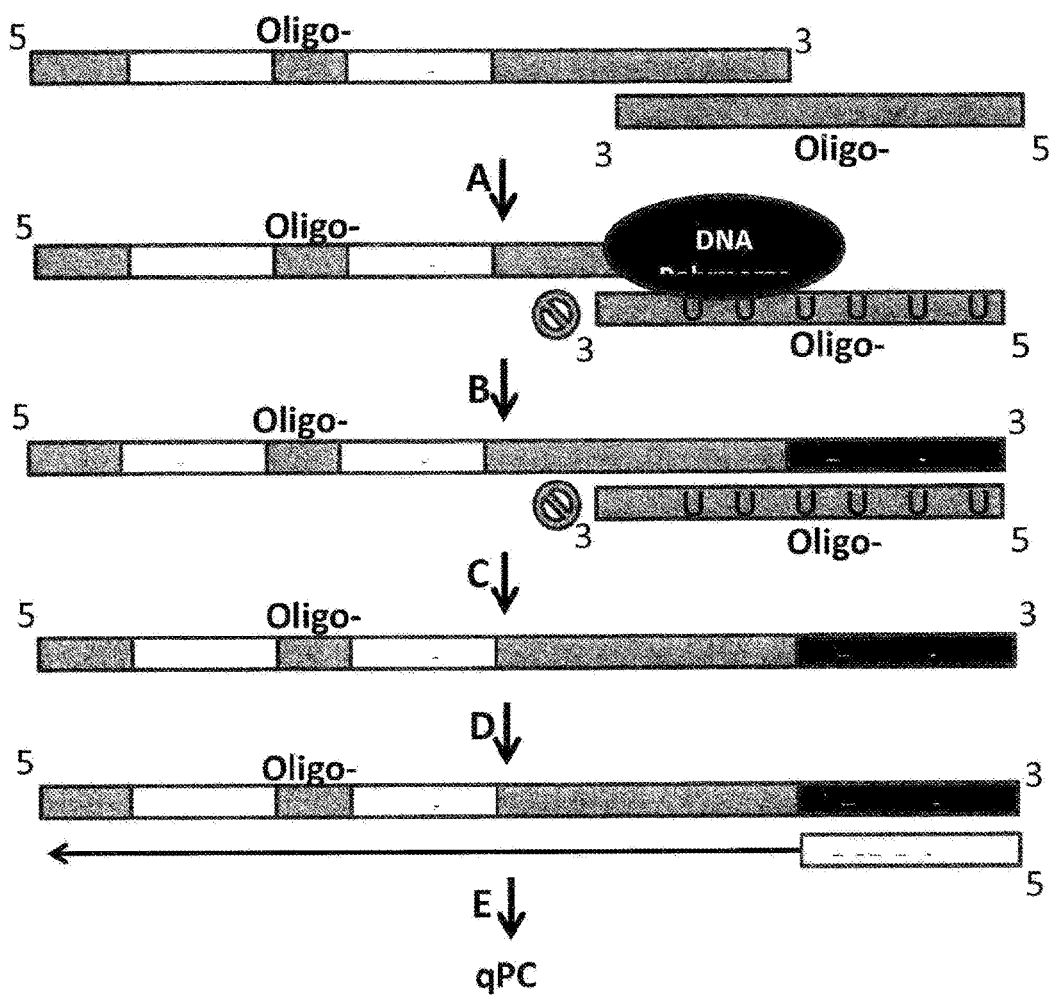

| Bacterial panel | Lower Limit Detected by DPE-PCR | $R^2$ (1e4-1e1 cfu) |
|---|---|---|
| Klebsiella pneumoniae | <10 | 0.9957 |
| Pseudomonas aeruginosa | <10 | 0.9860 |
| Enterobacter cloacae | <10 | 0.9995 |
| Acinetobacter baumannii | <10 | 0.9980 |
| Haemophilus influenzae | <10 | 0.9996 |
| Serratia marcescens | <10 | 0.9956 |
| Enterococcus faecalis | <10 | 0.9963 |
| Enterococcus faecium | <10 | 0.9899 |
| Streptococcus pyogenes | <10 | 0.9945 |
| Streptococcus agalactiae | <10 | 0.9969 |
| Streptococcus pneumoniae | <10 | 0.9999 |
| Staphylococcus epidermidis | <10 | 0.9990 |

| Candida panel | Lower Limit Detected by DPE-PCR | $R^2$ (1e5-1e3 cfu) |
|---|---|---|
| Candida albicans | ≈20 | 0.9945 |
| Candida tropicalis | ≈20 | 0.9969 |
| Candida glabrata | ≈40 | 0.9111 |
| Candida parapsilosis | ≈20 | 0.9950 |
| Candida krusei | ≈15 | 0.9868 |

DNA POLYMERASE ACTIVITY ASSAYS AND METHODS ENABLING DETERMINATION OF VIABLE MICROBES

CROSS REFERENCE TO RELATED APPLICATION

This application is a non-provisional application, which incorporates by reference herein and claims priority of U.S. Provisional Application No. 61/583,568, filed Jan. 5, 2012.

BACKGROUND OF THE INVENTION

The reference numbers used in this section and throughout this disclosure refer to the documents set forth in the "References" section herein.

DNA polymerase activity is indispensable for genome replication and organism propagation across all biological domains (1-3). Since its initial characterization (4), the ability to harness DNA polymerase activity in vitro has become a fundamental tool in the field of molecular biology research (5). Above and beyond its established importance in research, in vitro measurement of DNA polymerase activity potentially offers numerous useful applications within the pharmaceutical and clinical setting. For instance, since bacterial DNA polymerase is actively being targeted for development of novel antimicrobial agents (6, 7), a rapid and sensitive assay capable of measuring DNA polymerase activity is desirable. Also, loss or gain of DNA polymerase activity is intimately involved in human disease. For example, emerging links between DNA polymerase activity and genetic aberrations are designating the enzyme as a target for anti-cancer therapies (8, 9). Deficiencies in DNA polymerase activity have also been linked to mitochondrial disorders (10). Furthermore, measurement of DNA polymerase activity has the potential to be used as a rapid and sensitive diagnostic tool, capable of detecting virtually any organism harboring active DNA polymerase within a given environmental or biological matrix where sterility is expected.

The most common method used to measure DNA polymerase activity in vitro depends upon incorporation of radiolabeled nucleotides (11). However, routine use of such DNA polymerase assays is undesirable due to the inherent risks and restrictions associated with radioisotopes. Consequently, over the past few decades numerous non-radioactive in vitro polymerase assays have been developed. Some rely upon the measurement of fluorescence generated by DNA polymerase-mediated release of single stranded binding protein (12) or binding of PICOGREEN dsDNA reagent to double stranded DNA (13,14). Other methods rely on microplate coupling and detection of fluorescently-labeled nucleotides (15). More recently, molecular beacon-based (16) and electrochemical-based (17) DNA polymerase assays have been developed. Despite successfully averting the use of radioactivity, the above assays are limited by such factors as poor sensitivity, a small linear dynamic range of measurement, or the use of purified polymerase.

As will be apparent to those skilled in the relevant art, the measurement of DNA polymerase extension activity in accordance with the present invention as described herein represents a useful tool with far reaching applications such as, but not limited to, screening candidate-polymerase inhibitors in vitro, or detecting the presence any microbe (harboring active DNA polymerases) within a diverse range of sample types. This is a substantial improvement over the state of the present art, because if intended for these purposes, routine use of traditional polymerase assays that incorporate radiolabeled nucleotides is unattractive. Consequently, numerous non-radioactive DNA polymerase extension assays have been developed in recent decades. Despite successfully averting the use of radioactivity, current fluorescence-based DNA polymerase assays also suffer from various deficiencies. For example, detection of DNA polymerase activity via several existing non-radioactive assays is dependent upon the binding of PICOGREEN dsDNA reagent to newly-generated double stranded DNA (13,14). If intended to analyze DNA polymerase activity from freshly lysed organisms, PICOGREEN.-based assays would likely be hampered by background fluorescence via binding of PICOGREEN dsDNA reagent to genomic DNA. Microplate-based DNA polymerase assays have also been developed (15). Decreased sensitivity of microplate-based assays can be expected for numerous reasons, including dependence upon intermediate binding of either product or substrate to a microplate and/or inefficient incorporation of modified dNTPs by DNA polymerase. More recently, real-time measurement of DNA polymerase activity via molecular beacons has been described (16). Despite improved sensitivity, direct measurement of molecular beacon fluorescence could also potentially be hindered by exposure to crude cellular lysates.

SUMMARY OF THE INVENTION

The present invention improves upon the technology of the background art as described above, and provides a rapid, highly sensitive and quantitative assay, capable of measuring DNA polymerase extension activity from purified enzymes or directly from microbial lysates, including crude microbial lysates. The invention as described herein provides a significant and unexpected advancement toward sensitive detection of potentially any microorganism containing active DNA polymerase within a given sample matrix. The present invention involves methodology for enzymatic template generation and amplification (ETGA). Accordingly herein is described the first characterization of a novel ETGA methodology based upon the measurement of DNA polymerase extension activity coupled to a quantitative PCR readout. For the remainder of the disclosure herein, this type of diagnostic assay provided by the invention is referred to as DPE-PCR. The DPE-PCR assay of this invention can be used to measure low levels of purified enzyme and is capable of detecting endogenous DNA polymerase extension activity directly from microbial cell lysates.

BRIEF DESCRIPTION OF THE DRAWING FIGURES

FIG. 1 is a Schematic overview of a preferred DPE-PCR diagnostic assay in accordance with the present invention, and wherein: (Step A) DNA polymerase is incubated with a substrate consisting of pre-annealed Oligo-1 and Oligo-2. (Step B) During a 20 minute incubation at 37° C., DNA polymerase extends only the 3' end of Oligo-1. (Step C) 3 µL of the reaction mixture is subsequently placed into a hot start qPCR reaction containing uracil DNA glycosylase (UDG). Prior to activation of Taq, UDG degrades the deoxyuridine within Oligo-2, leaving only a single stranded product derived from polymerase-mediated extension of Oligo-1. (Step D) After activation of Taq, amplification is initiated via primer binding to the Oligo-1 extension product. (Step E) PCR cycling and detection via Taqman probe.

Figure 2:
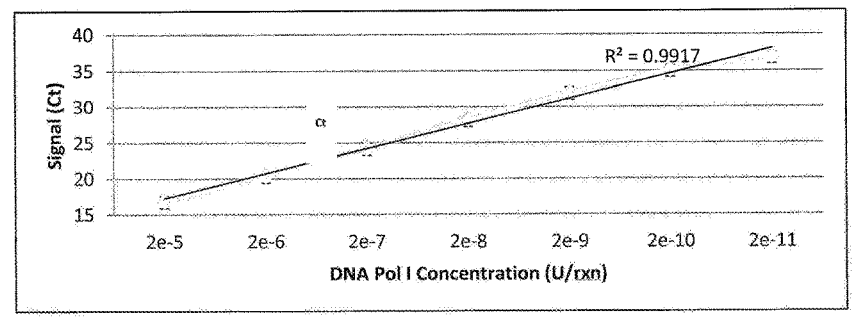
Figure 2:
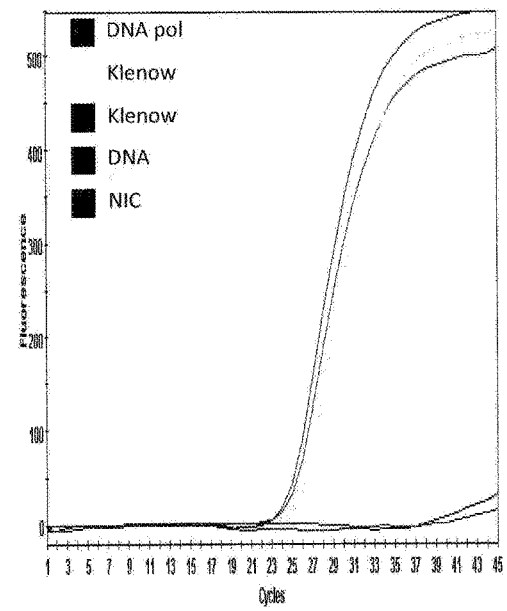
Figure 2:
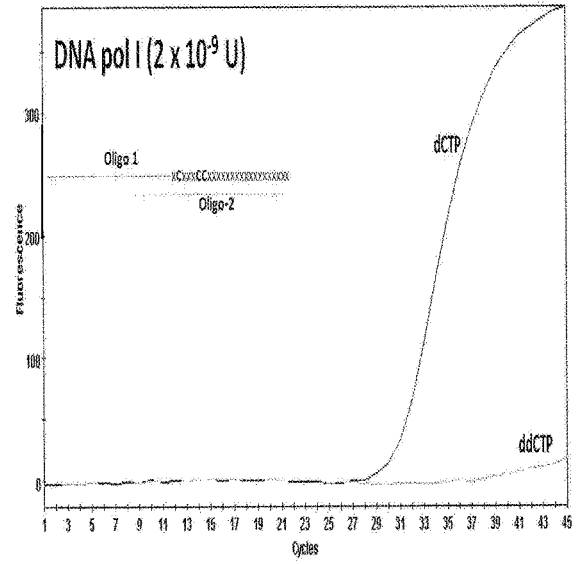

FIG. 2 is a schematic representation of the sensitive detection of purified DNA polymerase using DPE-PCR in accordance with a preferred embodiment of the present invention, and wherein: (A) A commercial source of DNA polymerase I was assayed in duplicate at 10 fold increments starting at $2\times10^{-5}$ Units (U) down to $2\times10^{-11}$ U per reaction. A representative DPE-PCR curve is shown for each polymerase input level and No Input Control (NIC). (B) A plot was constructed from n=4 data points per polymerase input level, taken from two independent experiments and linear regression analysis was performed (C) Triplicate reactions containing $2\times10^{-7}$ U of DNA polymerase I, Klenow, Klenow (exo-) and *E. coli* DNA Ligase were assayed in comparison to a NIC. A representative DPE-PCR curve is presented for each of the assayed enzymes and NIC (D) DPE-PCR signal was compared in reactions containing a dNTP mixture with either dCTP or ddCTP, a schematic representing the available sites for dCTP or ddCTP incorporation within the DNA substrate is presented adjacent to the DPE-PCR curves.

Figure 3:
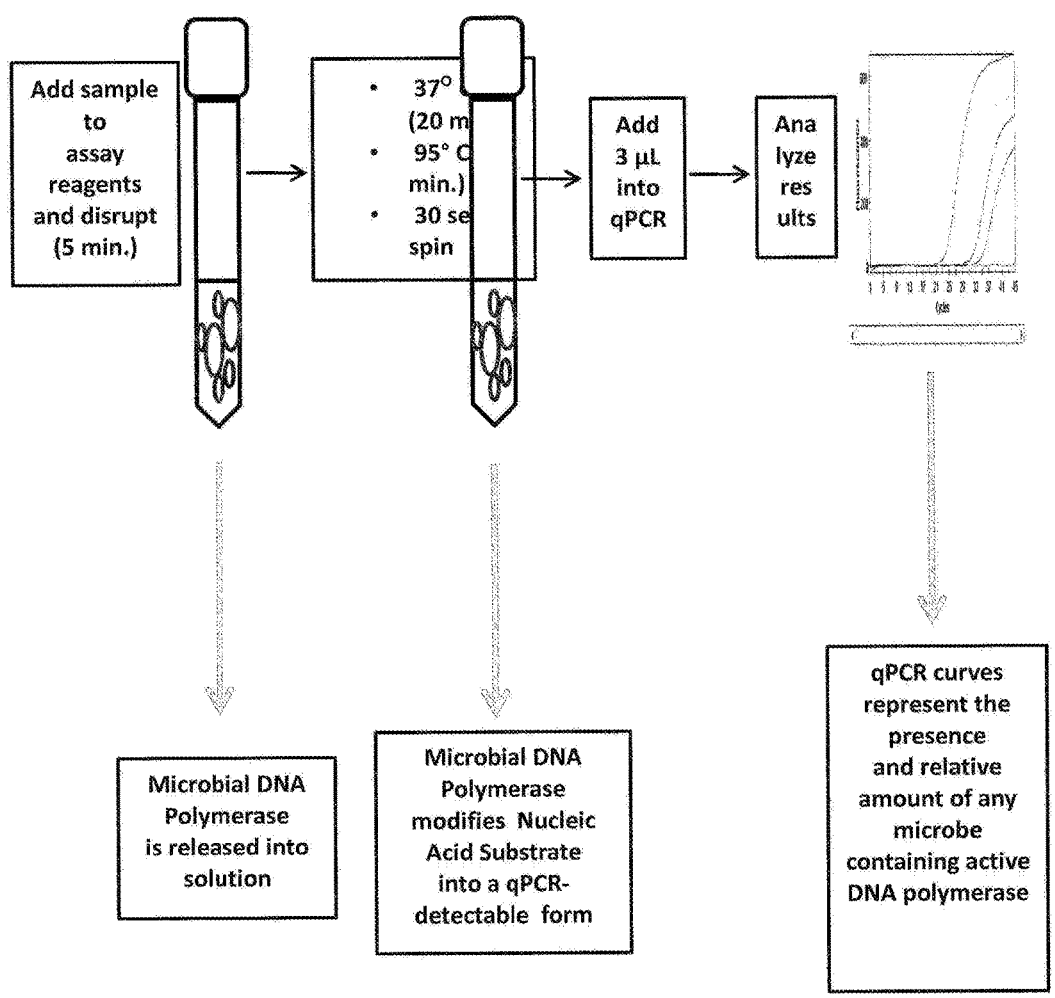

FIG. 3 is a schematic overview of coupling bead lysis to DPE-PCR in accordance with a preferred embodiment of the present invention.

Figure 4:
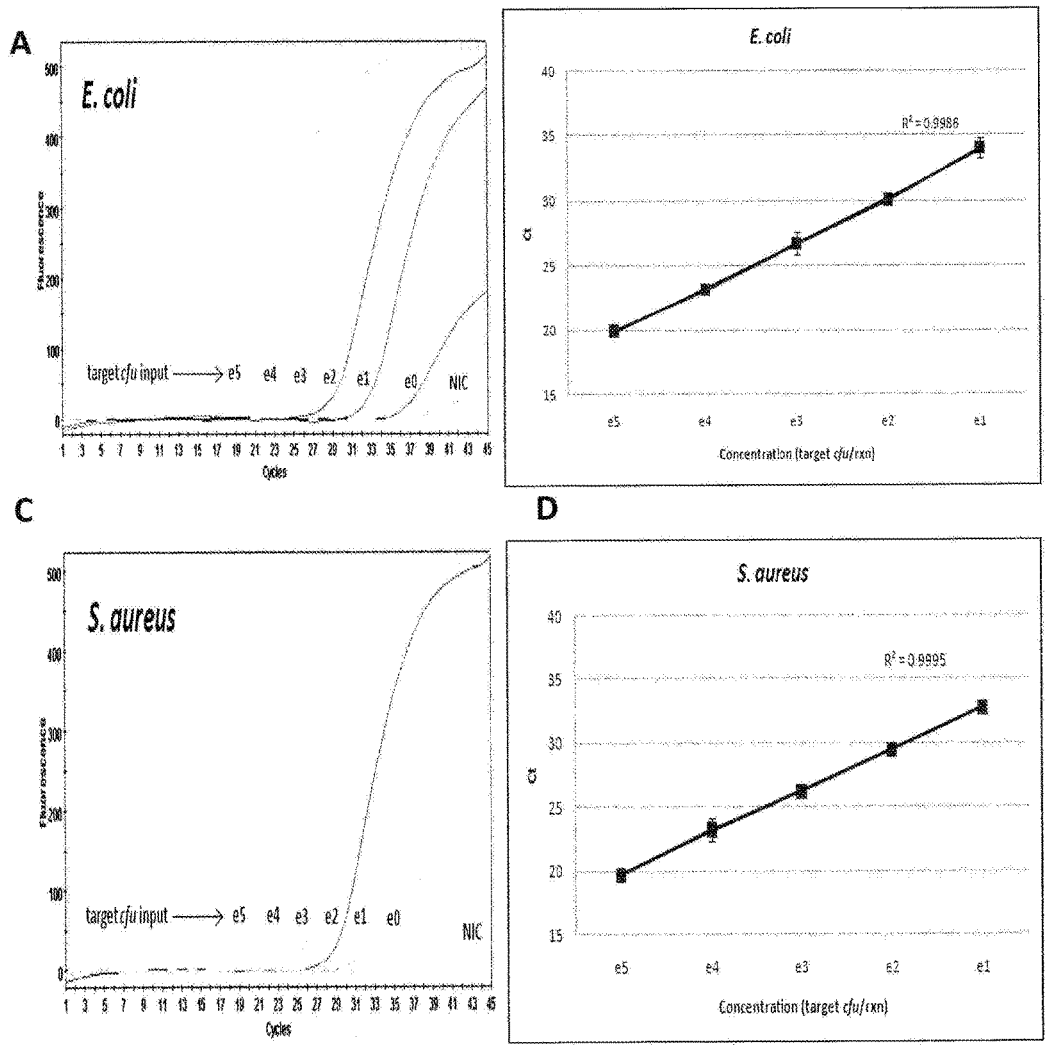

FIG. 4 is a graphical representation of how the performance of DPE-PCR in accordance with the present invention enables sensitive and quantitative detection of gram negative and gram positive bacteria via measurement of DNA polymerase extension activity in crude lysates, and wherein: (A) Decreasing amounts of *E. coli* cfu were spiked into bead lysis-coupled DPE-PCR. No Input Controls (NIC) were also included to monitor reagent background levels. All cfu spikes and NICs were performed in triplicate. A representative DPE-PCR curve is shown below for each level of bacterial input. Colony count plating and gsPCR were performed in an effort to obtain a better estimate of the actual cfu placed into each reaction and is presented in Supplemental FIG. 3 (B) A plot of *E. coli* DNA polymerase activity and linear regression analysis is presented. Graphs were generated using the average Ct values obtained from triplicate reactions of bacterial spikes ranging from $1\times10^5$-$1\times10^1$ input cfu. (C and D) cfu titration experiments were performed for *S. aureus* exactly as described above for *E. coli*. Colony count plating and gsPCR were performed in an effort to obtain a better estimate of the actual cfu placed into each reaction.

Figure 5:
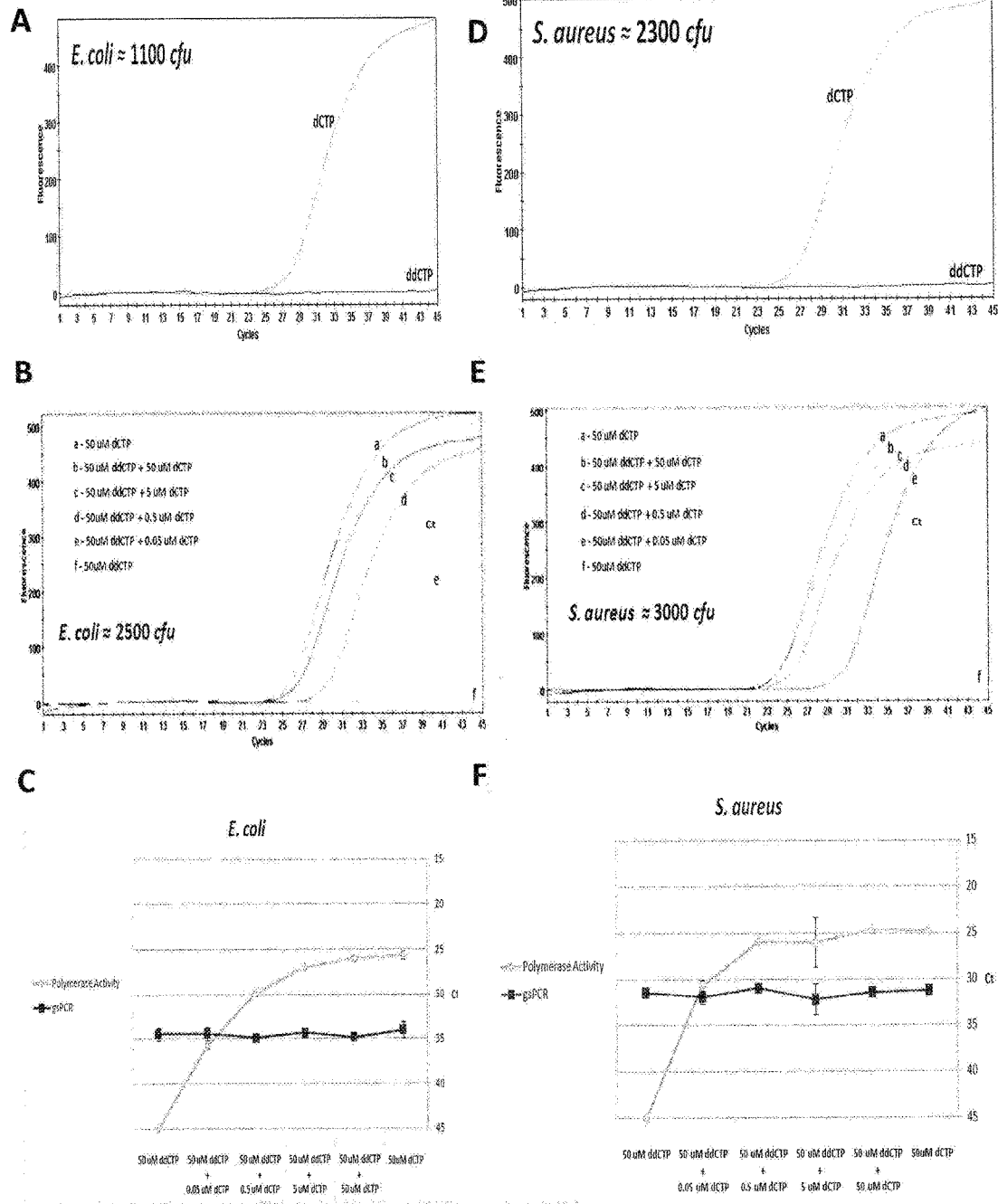

FIG. 5 shows a graphical representation of the detection of bacteria by DPE-PCR in accordance with another preferred embodiment of the present invention, and wherein: (A) 5 µL of *E. coli* suspension were added to bead lysis-coupled DNA polymerase assays comprised of a dNTP mix containing either 50 µM dCTP or 50 µM ddCTP. DPE-PCR curves representing *E. coli*-derived DNA polymerase activity is presented. Approximate cfu input as determined by plating is presented in the upper left region of the qPCR graph (B) 5 µL of *E. coli* suspension were added to bead lysis tubes containing 50 µL reaction buffer comprised of a dNTP mix with either 50 µM dCTP or 50 µM ddCTP. Prior to lysis, 1 µL of dCTP [2.5 mM, 0.25 mM 0.025 mM 0.0025 mM] was added to selected ddCTP-containing reactions. Reactions containing dCTP alone or ddCTP alone were run in parallel as "non-terminated" and "terminated" comparators. The resultant DPE-PCR curves representing *E. coli*-derived DNA polymerase activity is presented. Approximate cfu input as determined by plating is presented in the lower left region of the qPCR graph (C) *E. coli* gene specific PCR was also performed on the same lysates used for DNA polymerase detection presented in FIG. 2B. Linear plots of dCTP-dependent rescue of bacterial DNA polymerase detection vs. gsPCR of genomic DNA are shown. Plots were generated using the average qPCR Ct values from triplicate reactions at the indicated conditions (D-F) ddCTP termination and dCTP rescue experiments were performed for *S. aureus* exactly as described above for *E. coli*.

Figure 6:
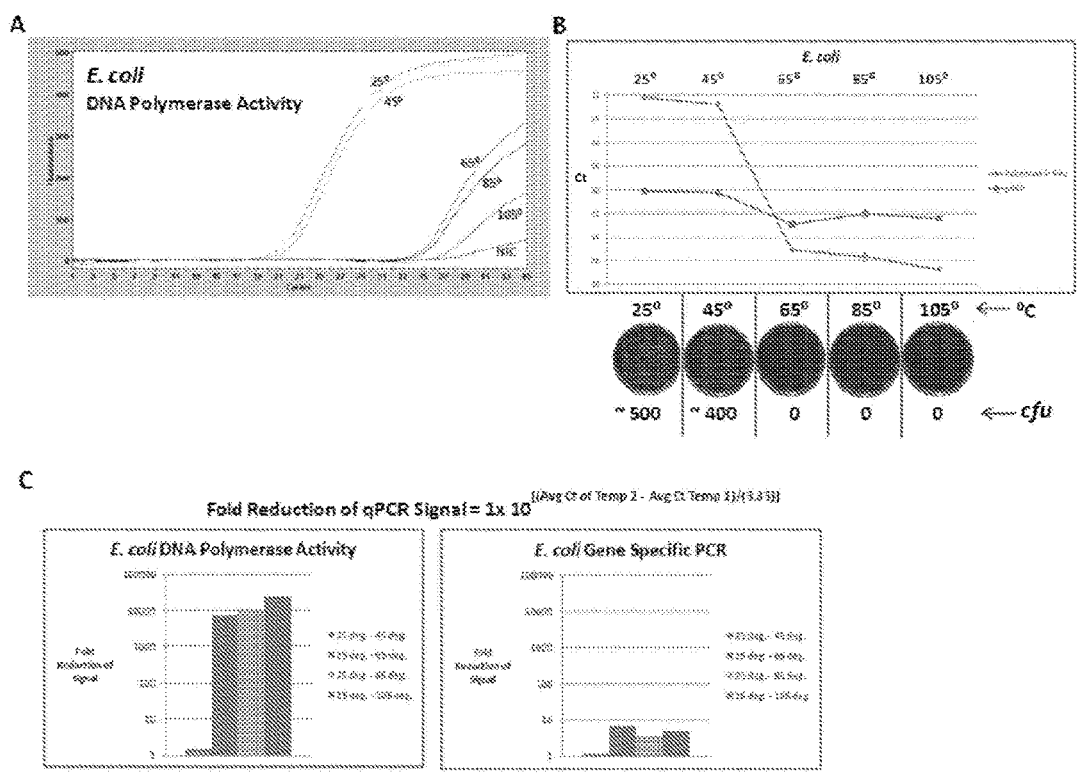

FIG. 6 is a graphical illustration of another embodiment of the present invention in which DPE-PCR ais an indicator of *E. coli* viability in response to heat treatment, and wherein: (A) 200 µL aliquots of an *E. coli* suspension (~2000 cfu/µL) were incubated at 25° C., 45° C., 65° C., 85° C. and 105° C. for 20 minutes. After heating, each bacterial stock was cooled to room temperature and 5 µL were transferred to the bead lysis-coupled DPE-PCR assay. DPE-PCR curves representing *E. coli*-derived DNA polymerase activity following each of the indicated temperature treatments are presented. (B) Plots were generated from triplicate DPE-PCR reactions and gsPCR of genomic DNA (from the same lysates) after the indicated temperature treatments of *E. coli* suspensions. Parallel plating was also performed in triplicate for each of the treated *E. coli* suspensions. Representative cfu monitoring plates are presented below the graph, revealing bacterial viability status after treatment at each temperature. (C) DPE-PCR is compared to gsPCR of genomic DNA in response to the various temperature treatments. "Fold Reduction of qPCR Signal" was calculated using the indicated equation and the values obtained were used to generate comparative bar graphs.

Figure 7:
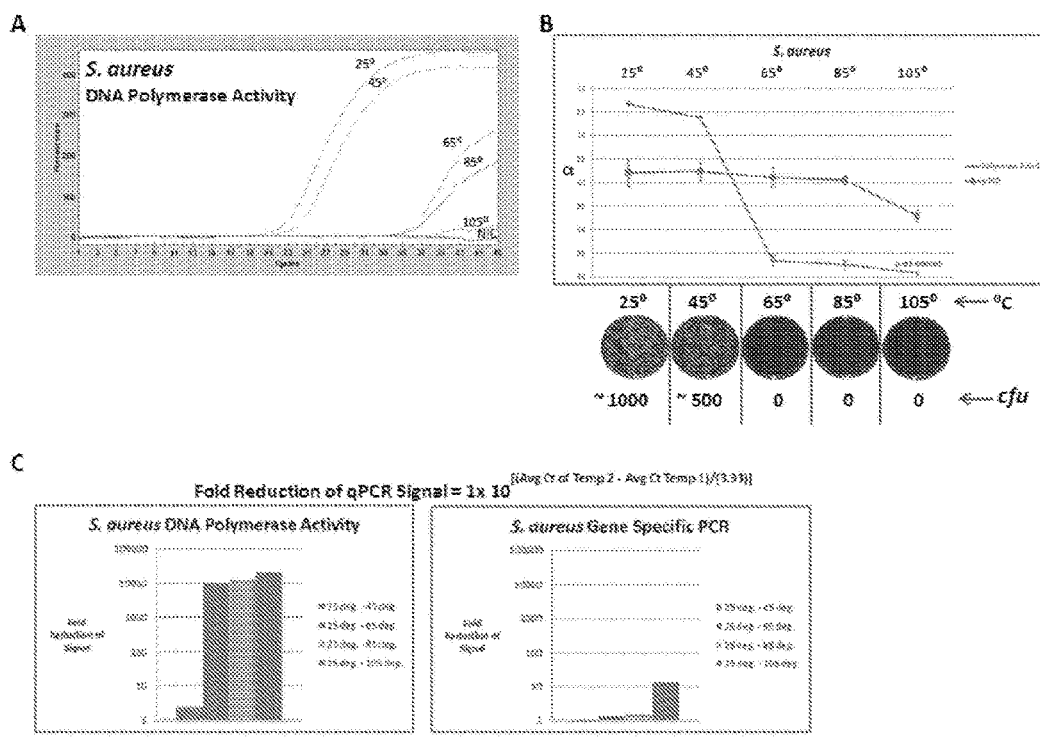

FIG. 7 is a graphical illustration of another embodiment of the present invention, in which DPE-PCR is an indicator of *S. aureus* viability in response to heat treatment, and wherein: (A) 200 µL aliquots of an *S. aureus* suspension (~2000 cfu/µL) were incubated at 25° C., 45° C., 65° C., 85° C. and 105° C. for 20 minutes. After heating, each bacterial stock was cooled to room temperature and 5 µL were transferred to the bead lysis-coupled DPE-PCR assay. DPE-PCR curves representing *S. aureus*-derived DNA polymerase activity following each of the indicated temperature treatments are presented. (B) Plots were generated from triplicate DPE-PCR reactions and gsPCR of genomic DNA (from the same lysates) after the indicated temperature treatments of *S. aureus* suspensions. Parallel plating was also performed in triplicate for each of the treated *S. aureus* suspensions. Representative cfu monitoring plates are presented below the graph, revealing bacterial viability status after treatment at each temperature. (C) DPE-PCR is compared to gsPCR of genomic DNA in response to the various temperature treatments. "Fold Reduction of qPCR Signal" was calculated using the indicated equation and the values obtained were used to generate comparative bar graphs.

FIG. 8 sets forth Table 1, as referred to herein, in which results are set forth showing the sensitive and linear detection of 17 additional clinically relevant microbial species in accordance with the teachings of the present invention.

DETAILED DESCRIPTION OF THE INVENTION

During the past fifty years, in vitro measurement of DNA polymerase activity has become an essential molecular biology tool. Traditional methods used to measure DNA polymerase activity in vitro are undesirable due to the usage of radionucleotides. Fluorescence-based DNA polymerase assays have been developed; however, they also suffer from various limitations. Herein is disclosed a rapid, highly sensitive and quantitative assay capable of measuring DNA polymerase extension activity from purified enzymes or directly from microbial lysates. When tested with purified DNA polymerase, the assay has been found to detect as little as $2\times10^{-11}$ U of enzyme (≈50 molecules), while demonstrating excellent linearity ($R^2=0.992$). The assay was also able to detect endogenous DNA polymerase extension activity down to at least 10 colony forming units of input gram-positive or gram-negative bacteria when coupled to bead mill lysis while maintaining an $R^2=0.999$. Furthermore, experimental evidence presented herein suggests that DNA polymerase extension activity is an indicator of bacterial viability, as demonstrated by the reproducibly strong concordance between assay signal and bacterial colony formation. Together, the novel methodology of the invention described herein represents a significant advancement toward sensitive detection of potentially any microorganism containing active DNA polymerase within a given sample matrix.

To further illustrate the foregoing concepts and advantages of the invention, the following examples are provided as illustrative of this invention, but are in no way to be construed as limitative thereof.

EXAMPLE

Materials and Methods:
DNA Substrate Preparation

The sequence of the DNA substrate (and qPCR primers presented below) was adapted from DNA oligos previously used to measure bacterial-derived ATP via T4 DNA ligase (18). Briefly, Oligo 1 and Oligo 2 (see FIG. 1) were pre-annealed and diluted to a working concentration of 0.01 µM.

DNA Polymerase Activity Reaction Using Commercial Polymerase

DNA Pol I (NEB cat #M0209L), Klenow (NEB cat #M0210S) and Klenow exo(−) (NEB cat #M0212S) were diluted to the indicated U/µL stock in Tris EDTA (T.E.) pH 8.0. To begin, 2 µL of DNA polymerase stock at each concentration were placed into a 50 µL polymerase assay mixture containing the following components: 50 µM dNTP, 20 mM Tris pH 8.0, 10 mM ammonium sulfate, 10 mM potassium chloride, 2 mM magnesium sulfate, 1% BSA, 0.1% Triton, 0.1% Tween, and 0.001 µM pre-annealed DNA substrate. Reactions were vortexed briefly and placed at 37° C. for 20 minutes. After 20 minutes, 3 µL of each reaction were immediately placed into a quantitative PCR (qPCR) reaction.

Detection by qPCR

The qPCR reaction master mix was prepared using the following components: LightCycler 480 Master Mix (Roche cat #04707494001), 333 nM of each primer, 166 nM Target probe (FAM), 166 nM internal control probe (TxRed), and 1.2 U of UDG (Bioline cat #BIO-20744). As a tool to monitor PCR inhibition, each qPCR reaction also included 40 copies of competitive internal control DNA. For each qPCR reaction, 3 µL of DNA polymerase reaction were added to 27 µL of master mix and a two-step qPCR was run on a SmartCycler (Cepheid, Sunnyvale Calif.) as follows: Initial incubation of 40° C. for 10 minutes and 50° C. for 10 minutes and at 95° C. for 5 minutes (to activate Taq), followed by 45 cycles of 5 s denaturation at 95° C. and 20 s annealing/extension at 65° C. Cycle threshold (Ct) values were generated automatically by the SmartCycler software using $2^{nd}$ derivative analysis of the emerging qPCR curves.

Bacterial Strains and Media

*Staphylococcus aureus* (ATCC 25923) and *Escherichia coli* (ATCC 25922) were used in this study. Cultures were grown in/on Brain-Heart Infusion liquid media/agar (Teknova.) The ATCC reference numbers and growth media for the additional 17 microorganisms tested are listed in FIG. 5.

Detection of Bacterial DNA Polymerase Activity Following Bead Mill Lysis

*S. aureus* and *E. coli* cultures were grown to an $OD_{600}$ of 1.0±0.2 (approximately $1\times10^9$ cfu/mL.) For each organism, 1 mL of culture was pelleted and washed three times in T.E. Bacterial suspensions were serially diluted in T.E., and 5 µL of each stock were added to bead lysis-reactions containing 50 µL of lysis-reaction buffer. A titration curve of $1\times10^5$ to $1\times10^0$ cfu/reaction was performed in triplicate for each organism, including triplicate reactions without bacterial suspension (No Input Control). After the addition of 5 µL bacterial stock (or No Input Control), lysis/reaction tubes were bead milled for 6 min. at 2800 rpm, followed by incubation at 37° C. for 20 min. After a 20 minute incubation, samples were heated to 95° C. for 5 min. and removed to cool at room temperature. Samples were then spun at 12 k×g for 30 seconds and 3 µL of each reaction were placed into qPCR. Five micro-liters of each bacterial stock was plated to obtain more accurate cfu input levels. Organism-specific PCR was also performed on the same lysates used for DNA polymerase detection. Primer and probe sequences for *S. aureus* and *E. coli* gene specific PCR are listed in FIG. 2.

Dideoxy Termination Experiments
Termination of Purified DNA Polymerase Extension Activity with ddCTP:

DNA polymerase assay reactions were prepared as described above with a dNTP mix containing either 50 µM dCTP or 50 µM ddCTP (Affymetrix #77332.) Reactions containing either dNTP mix were spiked with $2\times10^{-9}$ U of DNA polymerase I (New England Biolabs #M0209). Reactions were incubated at 37° C. for 20 minutes and 3 µL of each reaction were subsequently placed into qPCR.

Elimination of Microbial Detection Via ddCTP:

*S. aureus* and *E. coli* cultures were grown, washed and diluted as described above. To demonstrate ddCTP-dependent termination of microbial DNA polymerase, 5 µL of bacterial stock were added to bead lysis tubes containing 50 µL of reaction buffer with either 50 µM dCTP or 50 µM ddCTP. Lysis, incubation and qPCR were performed as described above. Five micro-liters of each bacterial stock were plated to determine more accurate cfu input levels. Gene specific PCR of genomic DNA was also performed on the same lysates used for DNA polymerase detection.

dCTP Rescue of Microbial Detection:

*S. aureus* and *E. coli* cultures were grown, washed and diluted as described above. Five micro-liters of bacterial stock were added to bead lysis tubes containing 50 µL of reaction buffer with 50 µM ddCTP. Prior to lysis, 1 µL of dCTP at 2.5 mM, 0.25 mM 0.025 mM 0.0025 mM was added to ddCTP-containing reactions. Reactions containing 50 µM dCTP alone and ddCTP alone were run in parallel as "non-terminated" and "terminated" comparators. Lysis, incubation and qPCR were performed as described above. Five micro-liters of each bacterial stock were plated to determine more accurate cfu input levels. Gene-specific PCR was also performed on the same lysates used for DNA polymerase detection.

Viability Assessment Experiments

*S. aureus* and *E. coli* cultures were grown, washed and diluted as described above. Two hundred micro-liters of bacterial stocks at approximately 2000 cfu/µL (in T.E.) were incubated at 25° C., 45° C., 65° C., 85° C. and 105° C. for 20 minutes. After heating, samples were cooled to room temperature and 5 μL of each bacterial stock were added to bead lysis tubes containing 50 IA of reaction buffer. Lysis, incubation and qPCR were performed as described above. Five micro-liters of each bacterial stock (treated at various temperatures) were also added to 1 ml of T.E. and 50 μL were plated for colony count determination. Gene specific PCR was also performed on the same lysates used for DNA polymerase detection.

Results and Discussion

In the development of the present invention, it was set out to develop a rapid, simple, highly sensitive and quantitative assay capable of measuring DNA polymerase extension activity derived from purified commercial sources or freshly lysed cells, which would improve upon and overcome the disadvantages of the foregoing described methodologies of the know art. FIG. 1 shows a schematic overview of the mechanisms involved in coupling DNA polymerase extension activity to qPCR. Notably, Oligo 2 (see FIG. 1, step C) is removed by uracil DNA glycosylase (UDG) prior to Taq activation, thus preventing non-specific extension of the substrate just prior to PCR cycling. A microbial detection method linking T4 DNA ligase activity to PCR amplification has been previously reported (18), which contains similarities to our DPE-PCR assay and is another example of an ETGA methodology. However, during the development of the present invention a modified version of this method, aimed at detecting NAD-dependent DNA ligase activity, suffered from various limitations (unpublished data), leading to the development of the novel DNA polymerase-based approach of the invention as described herein.

Sensitive and Linear Detection of Purified DNA Polymerase Extension Activity

An experiment was performed to determine the approximate analytical sensitivity of the DPE-PCR assay using commercially available DNA polymerase I. As shown in FIG. 2A, detection of DNA polymerase I was achieved over a wide range of input enzyme. In fact, measurement of DNA polymerase I extension activity is achieved down to as little as $2\times10^{-11}$ units (U) of enzyme (equivalent to approximately 50 molecules of polymerase). To our knowledge, detection of DNA polymerase extension activity at this level is unrivaled in existing DNA polymerase assays. In theory, this level of sensitivity could enable single microbe detection as *E. coli* has been reported to contain approximately 400 DNA polymerase I molecules per cell (11). Regression analysis also showed a strong positive linear correlation ($R^2$=0.992) between the DPE-PCR cycle threshold (Ct) values and units of input commercial DNA polymerase I after graphing data from two independent limit of detection experiments (FIG. 2B). After sensitivity and linearity experiments were performed, it was important to determine if the DPE-PCR assay signal was independent of intrinsic exonuclease activity. To this end, we subsequently compared signals generated by $2\times10^{-7}$ U of DNA polymerase I to those generated from DNA polymerase I lacking 5'→3' exonuclease activity (Klenow) and another version of the enzyme lacking all exonuclease activity (Klenow exo−). For additional specificity and background signal determination, *E. coli* DNA ligase at $2\times10^{-7}$ U and a No Input Control (NIC) were tested in parallel. As shown in FIG. 2C, both Klenow and Klenow exo—were detected at similar levels when compared to wild type DNA polymerase I, providing evidence that the DPE-PCR assay signal is derived from DNA polymerase-dependent extension and not intrinsic exonuclease activity. In addition to using exonuclease free polymerases, we set out to further demonstrate that DPE-PCR assay signal is derived from DNA polymerase-dependent extension of the DNA substrate prior to qPCR. Since incorporation of dideoxy nucleotides is a well-established method used for termination of DNA polymerase chain extension activities (19,20), we chose to substitute dCTP with dideoxyCTP (ddCTP) within our reaction mix. The schematic shown in FIG. 2D reveals the first possible position within the substrate that ddCTP can be incorporated by DNA polymerase. If ddCTP is incorporated into this position, the extension product of Oligo 1 would be insufficient in length for subsequent detection by qPCR primer 1 (FIG. 1). As shown in FIG. 2D, substitution of dCTP with ddCTP eliminates signal generated by DNA polymerase I, thus demonstrating that the DPE-PCR assay signal is dependent upon DNA polymerase extension of the substrate prior to qPCR. The presence of a low copy internal amplification control confirms that qPCR was not inhibited by the presence of low amounts of ddCTP that are carried over from the DNA polymerase assay reagents (Supplemental FIG. 1C). In addition, we feel it is important to note that we have sporadically observed a weak, but detectable signal in the absence of input-DNA polymerase (No Input Control). Due to the exquisite sensitivity of the DPE-PCR assay, we have demonstrated that weak background noise signals can be derived from several potential sources such as, but not limited to, DNA polymerase contamination present in the reagents prior to reaction assembly, DNA polymerase introduced by the operator during experimental setup and/or incomplete degradation of Oligo 2 (FIG. 1) prior to activation of Taq (unpublished data). Notably, these irregular sources of background noise are controllable by instituting stricter reagent preparation procedures and good aseptic technique.

Sensitive Universal Detection of Microbes Via Measurement of Endogenous DNA Polymerase Extension Activity Directly from Cell Lysates In addition to detecting purified polymerase activity, a simple universal method that measures microbial-derived DNA polymerase activity would be highly desirable. If achieved, such a method could enable the screening of candidate antimicrobial agents in actively growing cultures, thus allowing comparison of DNA polymerase extension activity to organism proliferation. Additionally, measurement of DNA polymerase extension activity could be used to screen environmental or biological samples for the presence of any microorganism harboring active DNA polymerase. To this end, we developed a simple method that couples microbial lysis to a DPE-PCR assay provided by the invention. As shown in FIG. 3, a liquid sample known to contain, or suspected of containing, microbes is added to a bead mill lysis tube, disrupted and immediately transitioned into the DPE-PCR assay. We chose one gram negative bacteria (*E. coli*) and one gram positive bacteria (*S. aureus*) to demonstrate the ability of our assay to measure microbial-derived DNA polymerase extension activity in crude cellular lysates. As shown in FIG. 4A, when linked with bead mill lysis, the DPE-PCR assay is capable of detecting a wide dynamic range of input *E. coli*, down to and below 10 colony forming units (cfu) per lysis tube. Linear regression analysis of *E. coli* detection was also performed down to 10 cfu of input bacteria and showed a strong positive linear correlation between input cfu and DNA polymerase extension activity signal as indicated by an $R^2$ value of 0.999 (FIG. 4B). Colony count plating and *E. coli*-gene specific qPCR (gsPCR) were run in parallel, confirming both the input level of cfu per reaction and the ability to monitor intact genomic DNA from the exact same lysates. DNA polymerase extension activity from *S. aureus* lysates was detected to a similar input level (FIG. 4C). S. aureus detection was plotted down to 10 cfu of input bacteria and also showed a strong linear correlation between input cfu and DNA polymerase extension activity signal ($R^2=0.999$, FIG. 4D). Colony count plating and gsPCR were performed in parallel to confirm the amount of S. aureus present in each bead lysis tube, as well as the presence of directly analyzable genomic DNA. Complete tables of plating, gsPCR and DNA polymerase activity results for both E. coli and S. aureus can be found in FIGS. 3 and 4. We subsequently tested the ability of the DPE-PCR assay to measure DNA polymerase activity from seventeen additional clinically relevant microorganisms. As shown in Table 1, we were able to detect DNA polymerase activity from all seventeen additional organisms including six gram-negative bacteria, six gram-positive bacteria and five Candida species. Detection of the seventeen additional microbes exhibited a strong positive linear correlation to input cfu with impressive low limits of detection. To date, and without failure we have similarly tested and detected a total of 31 different microbial species (data not shown). The upper linear dynamic ranges have yet to be fully characterized. More results containing parallel plating data and DPE-PCR results for each of 17 additional microbes are presented in FIG. 8. Together, these data support the notion that the performance of DPE-PCR in accordance with the teachings of the present invention has the potential to be useful as a universal "pan" test for the sensitive detection of any microbe in a normally sterile environment.

As shown in FIG. 2D, substitution of dCTP with ddCTP in the reaction mix represents a powerful tool for blocking the detection of DNA polymerase-dependent extension activity within our assay. To demonstrate that the signal derived from bacterial spikes was dependent upon their DNA polymerase extension activity, and not the other endogenous bacterial enzyme activities present in the lysates, we set up an experiment to compare DPE-PCR signals obtained from E. coli and S. aureus using a standard DNA polymerase reaction mix containing (dATP,dTTP, dGTP, dCTP) versus a reaction mix containing (dATP,dTTP, dGTP, ddCTP). As shown in FIG. 5A, when compared to the standard reaction mix, substitution of ddCTP blocked the generation of signal derived from E. coli cfu spikes (FIG. 5A). A dCTP rescue experiment was subsequently performed by comparing DNA polymerase extension activity from bacteria lysed in a reaction mix containing 100% ddCTP (50 µM), to those containing 50 µM ddCTP spiked with increasing amounts of dCTP (see materials and methods for a detailed description of rescue experiments). FIG. 5B demonstrates the rescue effect that increasing amounts of dCTP has on quantifiable DNA polymerase extension activity derived from E. coli lysates. In addition to measuring microbial DNA polymerase extension activity, gsPCR was run in parallel to verify that equivalent amounts of E. coli were present in each of the assayed lysates. A graphical comparison of DNA polymerase activity versus presence of genomic DNA is presented in FIG. 5C. Signal termination (via ddCTP) and dCTP rescue experiments were subsequently repeated with S. aureus and similar results were obtained (FIG. 5D-F). Tables containing DPE-PCR and gsPCR data for both E. coli and S. aureus can be found in FIGS. 6 and 7. qPCR internal control values are provided to demonstrate that low levels of ddCTP carried over into qPCR are not inhibitory, and thus are not responsible for the disappearance of DNA polymerase activity signal (FIGS. 6A and 7A). Together, the data presented in FIG. 5 strongly support the claim that the DPE-PCR assay is specifically detecting microbial DNA polymerase extension activity and signal is not derived from substrate modification via enzymatic activities other than DNA polymerase.

Measurement of DNA Polymerase Extension Activity as an Indicator of Bacterial Viability Traditional methods for determining bacterial viability are dependent upon growth and visualization of a particular microbe on solid medium (21). Although bacterial growth and visualization is the current industry gold standard, the traditional cfu viability determination methods are undesirable due to the length of time required for cfu formation. Furthermore, the ability to grow on solid media or in liquid culture can vary dramatically from one microbe to another, thus potentially limiting the detection of certain fastidious organisms (22). Due to the aforementioned limitations of traditional methods, there is a growing need in a wide variety of pharmaceutical (23), environmental, food processing and clinical testing arenas for the rapid assessment of microbial viability. Consequently, numerous molecular methods have been developed in an effort to quickly assess microbial viability status within a given matrix (24). Despite being rapid and sensitive, molecular methods that detect the presence of nucleic acid often fall short of representing an accurate measurement of cell viability. For example, amplification of endogenous DNA or RNA is a poor indicator of bacterial viability, due to the persistence of nucleic acid after cell death (25, 26). We set out to determine the feasibility of using DNA polymerase extension activity as an indicator of bacterial viability. To this end, an experiment was designed to compare detection of DNA polymerase extension activity and PCR-mediated detection of genomic DNA as indicators of bacterial viability following various amounts of heat treatment. To begin, E. coli suspensions were treated at increasing temperatures for a fixed period of time. After heat treatment, bacteria were subsequently assayed for the presence of both DNA polymerase extension activity and genomic DNA. Heat treated and non-heat treated bacterial stocks were also plated in parallel to monitor bacterial viability via the presence of visible cfu. FIG. 6A represents the levels of E. coli DNA polymerase extension activity measured after the indicated amounts of heat treatment. Notably, a significant drop in E. coli DNA polymerase extension activity was observed after incubation of bacterial suspensions between 45° C. and 65° C. (FIG. 6A). In contrast, gsPCR signal obtained from the same lysates remained relatively constant at all temperatures and is graphically compared to DNA polymerase activity in FIG. 6B. Plating results presented below the graph further demonstrate that increasing levels of heat treatment are sufficient to prevent cfu formation and are paralleled by a dramatic loss of DNA polymerase activity; however, dead cells still contribute genomic DNA levels very close to their original input levels confirming that gsPCR is a poor indicator of the presence of viable cells (FIG. 6B). In FIG. 6C, the bar graphs further highlight the relative abilities of DPE-PCR and gsPCR to monitor the disappearance of cfu in response to lethal amounts of heat treatment. Subsequently, we wanted to test whether measurement of DNA polymerase extension activity could be used to indicate the viability status of a gram positive organism as well. The previous E. coli experiments were repeated with S. aureus under the same conditions.

FIG. 7A-C show similar results obtained from heat treatment experiments repeated with S. aureus. Collectively, the strong concordance between the presence of cfu and DNA polymerase extension activity shown in FIGS. 4, 6, 7, and Table 1 of FIG. 8, demonstrates that DPE-PCR performed according to this invention has potential to be used as a general indicator of cell viability, and may additionally present the possibility of measuring DNA polymerase extension activity from microbes exposed to other clinically or pharmaceutically relevant agents (bacteriostatic and bactericidal) aimed at reducing cell proliferation or viability.

In summary, in accordance with the present invention there has been developed a novel, highly sensitive, quantitative and rapid DPE-PCR assay. In addition to quantitative detection of extremely low levels of purified enzyme, we have demonstrated the ability of DPE-PCR to reproducibly measure DNA polymerase extension activity from less than 10 cfu of bacteria via coupling to bead lysis. We have also demonstrated the potential for DPE-PCR to universally detect microbes by testing a panel of microorganisms comprised of seven gram-negative bacteria, seven gram-positive bacteria and five *Candida* species. Furthermore, preliminary evidence that the DPE-PCR assay can be used to assess bacterial viability was provided via the reproducibly strong correlation between DNA polymerase extension activity and proliferation as indicated by the presence of cfu. Considering the data disclosed herein, it is presently believed that the novel methods and techniques of the invention such as the preferred DPE-PCR assay as disclosed herein, has the potential to become a useful tool for a wide range of testing applications within pharmaceutical, environmental, food and clinical settings.

The contents of all references, patents and published patent applications cited throughout this application, are incorporated herein by reference to the same extent as if each individual publication, patent or patent application was specifically and individually indicated to be incorporated by reference.

The foregoing detailed description has been given for clearness of understanding only and no unnecessary limitations should be inferred therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for performing a diagnostic assay for the detection of the presence or amount of a microorganism within a sample matrix containing active DNA polymerase by the measurement of DNA polymerase extension activity, which assay comprises the steps of:
   (a) incubating DNA polymerase in the sample matrix with a substrate comprising two preannealed oligonucleotides wherein one of said oligonucleotides contains deoxyuridine nucleosides;
   (b) performing PCR cycling;
   (c) and detection via the use of a selected suitable-nucleic acid probe, thereby to detect endogenous DNA polymerase extension activity in the sample matrix as an indication of the presence or amount of said microorganism.

2. The method of claim 1, wherein measurement of DNA polymerase extension activity is an indicator of bacterial viability in said sample matrix.

3. The method of claim 1, wherein the sample matrix is serum.

4. The method of claim 1, wherein the sample matrix is plasma.

5. The method of claim 1, wherein the sample matrix is selected from the group consisting of purified enzymes, microbial lysates and crude microbial lysates.

6. The method of claim 1, wherein the assay specifically detects microbial DNA polymerase extension activity and signal is not derived from modification of said substrate via enzymatic activities other than DNA polymerase.

7. The method of claim 5, wherein prior to the performance of the assay, the method comprises the additional step of adding a microbial lysate or crude microbial lysate known to contain, or suspected of containing, a microorganism to a bead mill lysis tube, disrupting the microorganism cells and transferring the disrupted cells into the incubation step of the assay.

8. The method of claim 6, comprising the further step of adding a blocking agent to the sample mixture.

9. The method of claim 1, wherein the sample matrix is a biological sample.

10. The method of claim 1, wherein the sample matrix is an environmental sample.

* * * * *